(12) United States Patent
Buensuceso et al.

(10) Patent No.: US 9,579,348 B2
(45) Date of Patent: Feb. 28, 2017

(54) ENCAPSULATED KIDNEY TISSUE

(71) Applicant: Depuy Synthes Products, Inc., Raynham, MA (US)

(72) Inventors: Charito S. Buensuceso, North Brunswick, NJ (US); David C. Colter, Hamilton, NJ (US); Brian C. Kramer, Plainfield, NJ (US); Agnieszka Seyda, North Brunswick, NJ (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/252,132

(22) Filed: Apr. 14, 2014

(65) Prior Publication Data
US 2014/0271778 A1 Sep. 18, 2014

Related U.S. Application Data

(62) Division of application No. 12/337,413, filed on Dec. 17, 2008, now Pat. No. 8,734,527.
(Continued)

(51) Int. Cl.
A61K 35/22 (2015.01)
A61K 9/00 (2006.01)
(Continued)

(52) U.S. Cl.
CPC ............ A61K 35/22 (2013.01); A61K 9/0024 (2013.01); A61K 9/1652 (2013.01); A61K 9/48 (2013.01);
(Continued)

(58) Field of Classification Search
None
See application file for complete search history.

(56) References Cited

U.S. PATENT DOCUMENTS 4,352,833 A   10/1982   Young et al.
5,888,497 A    3/1999   Jain et al.
(Continued)

FOREIGN PATENT DOCUMENTS

EP    0 127 989       12/1984
WO    WO 96/27662      9/1996
(Continued)

OTHER PUBLICATIONS

In the U.S. Patent and Trademark Office, Non-Final Office Action in re: U.S. Appl. No. 12/337,413 dated Oct. 11, 2011, 7 pages.
(Continued)

Primary Examiner — Nashaat Nashed
Assistant Examiner — William W Moore
(74) Attorney, Agent, or Firm — Johnson & Johnson

(57) ABSTRACT

Provided are therapeutic implants comprising renal tissue encapsulated within a polymer bead. Also disclosed are methods for treating a disease state in a subject comprising implanting within said subject a therapeutic implant comprising renal tissue encapsulated within a polymer bead. Also provided are methods for making a therapeutic implant comprising: providing renal tissue; mixing the renal tissue with a solution comprising a polymer, thereby forming a tissue-polymer suspension; extruding the tissue-polymer suspension into an bead-forming solution, thereby forming a therapeutic implant comprising beads of said polymer within which the renal tissue is encapsulated.

8 Claims, 3 Drawing Sheets

Related U.S. Application Data

(60) Provisional application No. 61/015,328, filed on Dec. 20, 2007.

(51) Int. Cl.
  *A61K 9/16* (2006.01)
  *A61K 9/48* (2006.01)
  *A61L 27/34* (2006.01)
  *A61L 27/36* (2006.01)
  *A61K 35/12* (2015.01)

(52) U.S. Cl.
  CPC ............ *A61K 35/12* (2013.01); *A61L 27/34* (2013.01); *A61L 27/3604* (2013.01); *A61L 27/365* (2013.01); *A61L 27/3683* (2013.01)

(56) References Cited

U.S. PATENT DOCUMENTS

| | | | |
|---|---|---|---|
| 5,908,623 | A | 6/1999 | Baetge et al. |
| 6,465,001 | B1 | 10/2002 | Hubbell et al. |
| 6,776,985 | B1 | 8/2004 | Saller et al. |
| 7,780,993 | B2 | 8/2010 | Reisner et al. |
| 7,790,193 | B2 | 9/2010 | Melvik et al. |
| 8,734,527 | B2 * | 5/2014 | Buensuceso et al. ..... 623/23.73 |
| 2002/0115215 | A1 * | 8/2002 | Wolffe et al. .................. 435/455 |
| 2004/0171132 | A1 * | 9/2004 | Wild et al. .................. 435/235.1 |
| 2006/0251630 | A1 | 11/2006 | Stewart et al. |
| 2007/0086986 | A1 * | 4/2007 | Vigo ................... A61K 9/5036 424/93.7 |

FOREIGN PATENT DOCUMENTS

| | | |
|---|---|---|
| WO | WO 2009/085850 A2 | 7/2009 |
| WO | WO 2009/085850 A3 | 4/2010 |
| WO | WO 2009/085850 R | 6/2010 |

OTHER PUBLICATIONS

In the U.S. Patent and Trademark Office, Final Office Action in re: U.S. Appl. No. 12/337,413 dated Mar. 16, 2012, 10 pages.
In the U.S. Patent and Trademark Office, Final Office Action in re: U.S. Appl. No. 12/337,413 dated Apr. 29, 2013, 10 pages.
Bergers, G. et al.,"Cell Factories for Fighting Cancer," *Nature Biotechnology*, 2001; 19:20-21.
Bittner, B., et al., "Recombinant Human Erythropoietin (rhEPO) Loaded poly(lactide-co-glycolide) Microspheres: influence of the Encapsulation Technique and Polymer Purity on Microsphere Characteristics," *European Journal of Pharmaceutics and Biopharmaceutics*, 1998; 45:295-305.
Bloch, J. et al., "Neuroprotective Gene Therapy for Huntington's Disease, using Polymer-Encapsulated Cells Engineered to Secrete Human Ciliary Neutrophic Factor: Results of a Phase I Study," *Human Gene Therapy*, 2004; 15:968-975.
Brines, M. and Cerami, A., "Discovering Erythropoietin's Extra-Hematopoietic Functions: Biology and Clinical Promise," *Kidney Int.*, 2006; 70(2):246-250.

Chong, Z.Z., et al., "Erythropoietin Is a Novel Vascular Protectant Through Activation of Akt1 and Mitochondrial Modulation of Cysteine Proteases," *Circulation*, 2002;106 (23):2973-2979.
Heald, K.A. et al., "Assessment of the reproducibility of alginate encapsulation of pancreatic islets using the MITT colorimetric assay", *Cell Transplant*, 994; 3(4):333-337 (Abstract only)., 1994.
Heim, W.G., "Effects of surgery and autologous tissue implantation on liver catalase activity of the mouse", *American Journal of Physiology*, vol. 191, No. 1:23-24 (1957).
International Search Report dated Mar. 15, 2010, in PCT Application No. PCT/US2008/087211.
Joki, T. et al., "Continuous Release of Endostatin from Microencapsulated Engineered Cells for Tumor Therapy," *Nature Biotechnology*, 2001; 19:35-39.
Koo, J. et al., "Secretion of Erythropoietin from Microencapsulated Rat Kidney Cells: Preliminary Results," *International Journal of Artificial Organs*, 1993; 16(7):557-561.
Maysinger et al., "Microencapsulated Ciliary Neutrophic Factor: Physical Properties and Biological Activities," *Experimental Neurology*, 138, 177-188 (1996).
Merck Manual, 1987:1105.
Morlock. M., et al., "Erythropoietin Loaded Microspheres Prepared from Biodegradable LPLG-PEO-LPLG triblock Copolymers: Protein Stabilization and In -Vitro Release Properties," *Journal of Controlled Release*, 1998; 56:105-115.
Naffakh, N., et al., "Long-Term Secretion of Therapeutic Proteins from Genetically Modified Skeletal Muscles," *Human Gene Therapy*, 1996; 7(11):11-21.
Office Action issued in counterpart Japanese Application No. 2010-539742 dated Jul. 9, 2013 with English Translation.
Orive G., et al., "Long-Term Expression of Erythropoietin from Myoblasts Immobilized in Biocompatible and Neovascularized Microcapsules," *Molecular Therapy*, 2005; 12(2):283-289.
Pistel, K.F., et al., "Biodegradable Recombinant Human Erythropoietin Loaded Microspheres Prepared from Linear and Star-branched Block Copolymers: Influence of Encapsulation Technique and Polymer Composition on Particle Characteristics," *Journal of Controlled Release*, 1999; 59(3): 309-325.
Santhanam, A.V.R., et al., "Role of Endothelial NO Synthase Phosphorylation in Cerebrovascular Protective Effect of Recombinant Erythropoietin during Subarachnoid Hemorrhage-induced Cerebral Vasospasm," *Stroke*, 2005;36 (12):2731-2737.
Satoh, K., et al. "Important Role of Endogenous Erythropoietin System in Recruitment of Endothelial Progenitor Cells in Hypoxia-Induced Pulmonary Hypertension in Mice," *Circulation*, 2006; 113(11)1442-1450.
Search Report issued by the Intellectual Property Office of Singapore in related Application No. 201004179-6 dated Sep. 21, 2012.
Urao, N., et al., "Erythropoietin-mobilized Endothelial Progenitors Enhance Reendothelialization via Akt-Endothelial Nitric Oxide Synthase Activation and Prevent Neointimal Hyperplasia," *Circulation Research*, 2006; 98:1405-1413.
Written Opinion issued by the Intellectual Property Office of Singapore in related Application No. 201004179-6 dated Sep. 21, 2012.
Yeh, M.K., et al., "The Preparation of Sustained Release Erythropoietin Microparticle," *Journal of Microencapsulation*, 2007; 24(1):82-93.

* cited by examiner

ENCAPSULATED KIDNEY TISSUE

CROSS-REFERENCE TO RELATED APPLICATIONS

This application is a divisional application of U.S. patent application Ser. No. 12/337,413, filed Dec. 17, 2008 (now U.S. Pat. No. 8,734,527 (issued May 27, 2014)), which claims benefit to U.S. Provisional Patent Application No. 61/015,328, filed Dec. 20, 2007, the contents of which are incorporated by reference in their entirety.

FIELD OF THE INVENTION

The present invention pertains to the encapsulation of tissue in polymer.

BACKGROUND OF THE INVENTION

The kidney plays a critical role in maintaining physiological homeostasis. Among its homeostatic functions are acid-base balance, regulation of electrolyte concentrations, blood pressure and blood volume regulation. The kidneys accomplish these functions independently, as well as through coordination with other organ systems through the actions of hormones and proteins secreted into the bloodstream. These secreted proteins include erythropoietin (Epo), urodilatin, renin and vitamin D, as well as less emphasized proteins such as adiponectin and leptin.

Adiponectin (also known as AdipoQ, Acrp30, apM1, and GBP28) is an adipocyte-derived cytokine that has been shown to have anti-inflammatory properties. In addition, it functions to regulate blood glucose levels via cross-communication with the liver. Normal blood concentrations of adiponectin are 5-30 µg/ml in humans. Previous studies have shown that circulating levels of adiponectin are elevated during chronic caloric restriction in both humans and mice. In contrast, low levels of adiponectin in human plasma correlate with high insulin, glucose, and triglycerides, as well as increased obesity. It has been shown that over-expression of human adiponectin in transgenic mice resulted in suppression of fat accumulation and prevention of premature death by a high-calorie diet. Furthermore, a diabetes susceptibility locus has been mapped to chromosome 3q27, the location of the human adiponectin gene. Increasing adiponectin blood levels could have therapeutic value in treating diabetes and related comorbidities.

Leptin is a 16-kilodalton-protein hormone that plays a key role in regulating energy intake and energy expenditure by decreasing appetite and increasing metabolism. Recently, leptin has been shown to play a role in protecting the kidneys from renal injury in a mouse model of diabetic nephropathy. In addition, leptin promotes angiogenesis by up-regulating vascular endothelial growth factor.

For over thirty years, erythropoietin (Epo), a 30.4 kDa protein synthesized and secreted mainly by the kidney, has been successfully used to stimulate erythropoiesis in patients suffering from anemia. Recently, it has become apparent that the beneficial effects of EPO extend well beyond the stimulation of red blood cell production (Brines et al., *Kidney Int.*, 2006; 70(2):246-250). Previous studies by Chong et al. established that Epo protects the vascular endothelium against ischemic injury. Chong et al., *Circulation*, 2002; 106 (23):2973-9. Others have confirmed these findings, demonstrating that Epo has a protective effect on endothelial cells in diverse animal models of vascular disease (Santhanam et al., *Stroke*, 2005; 36 (12):2731-7; Satoh et al., *Circulation*, 2006; 113(11):1442-50; Urao et al., *Circulation Research*, 2006; 98(11):1405-13). In chronic renal failure, patients develop anemia due to inadequate Epo production by the kidney. Recombinant Epo, administered as a replacement therapy, restores hematocrit and blood hemoglobin concentrations, eliminating the need for blood transfusions. This treatment, however, entails regular injections of Epo, two to four times per week, given either intravenously or subcutaneously. Epo dosing is cumbersome, resulting in patient non-compliance and frequent, cyclical fluctuations in blood Epo and hematocrit values.

In light of the protective effects of Epo on the cardiovascular system, as well as the current challenges associated with recombinant Epo treatment, implantation of an Epo-eluting device may be an effective alternative to the current treatment modality. Such an implantable device might also better control hematocrit values and potentially even protect organ microvasculature from injury.

Recent studies focused on developing alternative Epo delivery systems are in progress. Investigators have demonstrated the feasibility of encapsulating recombinant Epo in different types of bioabsorbable polymers (See, e.g., Yeh et al., *J. Microencapsulation,* 2007; 24(1):82-93; Pistel et al., *J. of Controlled Release,* 1999; 59(3):309-325; Bittner et al., *European Journal of Pharmaceutics an Biopharmaceutics,* 1998; 45:295-305; Morlock et al., *Journal of Controlled Release,* 1998; 56:105-115). While encapsulation of peptides and small molecules into biodegradable envelopes can be achieved using several techniques, the encapsulation of proteins has associated challenges. For example, it has been difficult to obtain continuous Epo release profiles with minimal initial burst as well as sufficient protein loading within the microspheres. The development of a recombinant Epo-loaded, implantable device may require frequent drug-reloading or device replacement to ensure long-term, robust disease management.

Other investigators have placed less emphasis on recombinant Epo and are pursuing a genetic engineering and cell therapy approach. Naffakah et al. examined whether the secretion of Epo from genetically modified cells could represent an alternative to repeated injections for treating chronic anemia. Naffakh et al., *Human Gene Therapy,* 1996; 7(1):11-21. In this study, primary mouse skin fibroblasts were transduced with a retroviral vector in which the murine Epo cDNA was expressed under the control of the murine phosphoglycerate kinase promoter. These "Neo-organs" containing the genetically modified fibroblasts embedded into collagen gels were implanted into the peritoneal cavity of mice resulting in an increase in hematocrit and serum Epo concentrations after a 10-month observation period. The implantation of Epo-secreting fibroblasts represents a potential method for permanent in vivo Epo delivery.

Similarly, Orive et al. investigated the long-term functionality of an ex vivo gene therapy approach. Orive G et al., *Molecular Therapy,* 2005; 12(2):283-9. Polymer microcapsules loaded with Epo-secreting myoblasts were implanted into the peritoneum and subcutaneous tissue of syngeneic and allogeneic mice. High and constant hematocrit levels were maintained for more than 100 days in all implanted mice. Interestingly, the functionality of capsules implanted in the allogeneic mice persisted until day 210 after implantation. These results demonstrate the feasibility of cell encapsulation technology for the long-term delivery of Epo within an allogenic model.

In addition, many companies are also developing cell encapsulation technology. StemCells (CytoTherapeutics) is developing cell capsules that can be surgically implanted and release substances that cross the blood-brain barrier for neurological applications. Novocell Inc. (San Diego, Calif.) is developing encapsulated islet cells for insulin-dependent diabetes. Islet Technology, Inc. (St. Paul, Minn.) is also developing islet microencapsulation technology and has demonstrated the long-term persistence of their implants in a diabetic dog for more than 3 years. Amcyte Inc. (Santa Monica, Calif.) is developing islet cells to form an artificial pancreas using photocross-linkable alginate or polyethylene glycol capsule. Finally, MicroIslet Inc. (San Diego, Calif.) is developing a suspension of microencapsulated, porcine islets for injection into the abdominal cavity using a highly biocompatible alginate.

Indeed, several efforts exist, attempting to exploit cell and protein encapsulation as a means to deliver therapeutic agents. In total, the state-of-the-art has generated very compelling and useful data, and these efforts have demonstrated the utility of encapsulation as a method for the controlled, long-term delivery of Epo in vivo. However, there are considerable safety issues that must be resolved before the encapsulation of genetically modified cells can be utilized for therapeutic proposes.

There remains a need for implantable devices that overcome traditional problems associated with therapeutic deployment.

SUMMARY OF THE INVENTION

Provided are therapeutic implants comprising renal tissue encapsulated within a polymer bead. Also disclosed are methods for treating a disease state in a subject comprising implanting within said subject a therapeutic implant comprising renal tissue encapsulated within a polymer bead.

Also provided are methods for making a therapeutic implant comprising: providing renal tissue; mixing the renal tissue with a solution comprising a polymer, thereby forming a tissue-polymer suspension; extruding the tissue-polymer suspension into an bead-forming solution, thereby forming a therapeutic implant comprising beads of said polymer within which the renal tissue is encapsulated.

DETAILED DESCRIPTION OF ILLUSTRATIVE EMBODIMENTS

Figure 1:
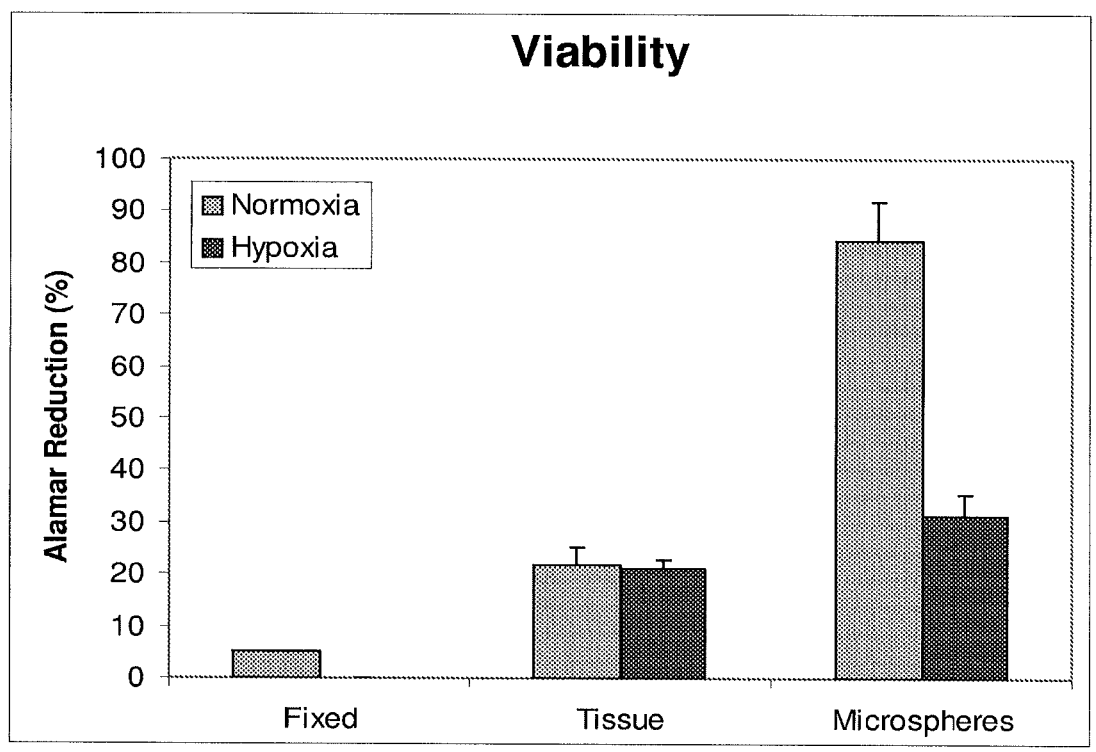
FIG. 1 depicts the results of an assessment of the relative viability of encapsulated and non-encapsulated minced rat kidney tissue.

Despite the increasing interest in cell encapsulation as a method for delivering therapeutic agents, sparse to no attention has been given to the encapsulation of whole tissue fragments. It has presently been discovered that the encapsulation of minced kidney tissue provides an opportunity to deliver natural Epo and other beneficial agents from endogenous cells, while providing an immunological barrier to prevent tissue rejection. As discovered herein, the transplantation of an inducible, beneficial agent-secreting, implantable device composed of kidney tissue can dramatically alleviate the current financial, safety, and medical issues surrounding erythropoiesis-stimulating agents. Kidney tissue encapsulation technology may also enable the development of other therapeutic technologies for the treatment of various disease states.

In the present disclosure the singular forms "a," "an," and "the" include the plural reference, and reference to a particular numerical value includes at least that particular value, unless the context clearly indicates otherwise. When values are expressed as approximations, by use of the antecedent "about," it will be understood that the particular value forms another embodiment. Where present, all ranges are inclusive and combinable.

Provided are therapeutic implants comprising renal tissue encapsulated within a polymer bead. The present implants are suitable for introduction in vivo and for providing therapeutic effects following implantation. The renal tissue for use in the present implants may be autologous tissue, allogeneic tissue, xenogeneic tissue, or any combination thereof. The renal tissue may be size-processed for use in the present implants, for example, by mincing a source of renal tissue into fragments. Such fragments may have a size of less than about 1 mm, or they may be larger. The size of the fragments is preferably measured in terms of the largest dimension thereof, e.g., lengthwise if the fragments have an aspect ratio of greater than 1:1, by the length of a side if the fragments are roughly cubical, or by diameter if the fragments are roughly spherical, etc. In addition to mincing, the fragments may be further size-processed to reduce the dimensions of the tissue. For example, the fragments may be further minced so that the size of substantially all of the fragments are less than about 300 µm, less than about 150 µm, less than about 100 µm, or less than about 50 µm. The total quantity of renal tissue in an implant of the present invention may be at least about 100 mg, at least about 50 mg, at least about 30 mg, or at least about 10 mg. Various factors, such as the desired total surface area of the renal tissue, the type of therapy, the type of renal tissue, the characteristics of the subject undergoing therapy, the type and stage of the disease state against which therapy is desired, the quantity and type of materials secreted by the tissue, and other factors that will be appreciated by those skilled in the art, may be used to determine the quantity of renal tissue in the implant, the size of the individual tissue fragments, or both.

The polymer bead preferably comprises a biocompatible polymer, such as a naturally occurring or synthetically derived biopolymer. The polymer bead may comprise such polymers as alginate, hyaluronic acid, carboxymethylcellulose, polyethylene glycol, dextran, agarose, poly-L-lysine, carageenan, pectin, tragacanth gum, xanthan gum, guar gum, gum arabic, type I collagen, laminin, fibronectin, fibrin, or any combination thereof. A preferred combination of polymers comprises alginate and poly-L-lysine. Such polymers are readily commercially available.

The term "bead" when used in reference to the polymer is intended to convey that the polymer composition generally assumes a roughly spherical shape, but may also be ovoid or oblong. The precise shape of the polymer bead is not essential to the present invention; any shape that permits the renal tissue to be substantially enveloped within the polymer is acceptable. When measured according to its greatest dimension, a polymer bead may have a diameter of about 0.5 mm to about 10 mm, and is preferably about 3 mm to about 6 mm. The size of the polymer bead may be measured according to the characteristics of the bead prior to implantation, or following implantation. As polymer beads may spontaneously bud, the size of the polymer bead may be measured with respect to an un-budded bead or with respect to a bead that results from budding.

The characteristics of the polymer bead permit the instant implants to secrete beneficial agents from within the bead into the ambient environment in which the bead is implanted or otherwise contained. In other words, the polymer bead is permeable to substances that are secreted by the renal tissue that is encapsulated within the bead. The renal tissue may be endogenous, naturally occurring tissue or may include cells that contain gene alterations, such as insertions of genes or portions of genes that are not naturally present. Renal tissue that includes gene alterations or insertions may be physically capable of secreting substances that endogenous or naturally occurring tissue cannot. The renal tissue and therefore in turn the implant of the present invention may secrete any compound that renal tissue, whether endogenous or altered (e.g., genetically altered) is physically capable of producing. For example, the renal tissue may secrete one or more hormones, prohormones, proteins, growth factors, trophic factors, or any combination thereof. As additional examples, and as further described herein, the tissue may secrete one or more of erythropoietin, MCP-1, adiponectin, leptin, and MMP-2. The compounds that genetically altered renal tissue may secrete are theoretically virtually limitless.

Also provided are methods for treating a disease state in a subject comprising implanting within the subject a therapeutic implant comprising renal tissue encapsulated within a polymer bead. Because the present implants are capable of secreting a number of beneficial agents, the inventive methods can be used to treat a wide variety of disease states. As used herein, "treatment" may refer to prophylactic therapy, or alleviation of any pathological phenotype. The disease state for which treatment is provided by the present invention may be anemia, stroke, cardiovascular disease, or any renal disease, i.e., any pathology that is directly or indirectly associated with improper kidney function, for example, which results in improper kidney function, or which is caused at least in part by improper kidney function. Renal disease may be hereditary, congenital, or acquired. Non-limiting examples of renal disease include polycystic kidney disease, Alport's syndrome, hereditary nephritis, primary hyperoxaluria, cystinuria, nephritis, nephritic syndrome, hypertension, diabetes, acute kidney disease, chronic kidney disease (persistent proteinuria), renal tubular acidosis, glomerular diseases, and Goodpasture's syndrome. The benefits of treatment with Epo, for example has been widely documented with respect to a number of pathologies, and is readily appreciated by those skilled in the art. The characteristics of the polymer beads and renal tissue for use in the present methods may be as previously described with respect to the inventive therapeutic implants.

The present invention is also directed to methods for making a therapeutic implant. The methods for making a therapeutic implant successfully results in the fabrication of therapeutic compositions that can be used in accordance with the present disclosure. The present methods comprise providing renal tissue; mixing the renal tissue with a solution comprising a polymer, thereby forming a tissue-polymer suspension; extruding the tissue-polymer suspension into a bead-forming solution, thereby forming a therapeutic implant comprising beads of the polymer within which the renal tissue is encapsulated.

Renal tissue may be prepared in accordance with the previously disclosed techniques, including selecting a tissue type and size-processing. The polymer solution with which the renal tissue is mixed in accordance with the present invention may comprise a combination of a polymer and a growth medium. The characteristics of the polymer may be determined as described above. Any acceptable culture medium, nutrient broth, or the like may be used for the instant growth medium; the characteristics of an appropriate growth medium, which may comprise a mixture of media, are readily determined by those skilled in the art. Growth media can vary in pH, glucose concentration, growth factors, and the presence of other nutrient components, but the growth medium should fulfill at least some of the nutritional requirements of the renal tissue, and preferably fulfills most or all nutritional requirements, and should possess pH and other chemical characteristics necessary to sustain and nurture the renal tissue. An example of a suitable growth medium is DULBECCO'S MODIFIED EAGLES MEDIUM (DMEM; Invitrogen, Carlsbad, Calif.). Growth media are commercially available and suitable media are readily recognized by those skilled in the art. To prevent infection, antibiotics, such as penicillin, streptomycin, and the like, may be added to the growth medium. Serum, such as fetal bovine serum, may also be added to the growth medium.

Mixing of the renal tissue and the polymer solution may be achieved by any means that are suitable for forming a suspension, i.e., a mixture in which the renal tissue is substantially uniformly suspended in the polymer solution, such as agitation, stirring, or pouring. For example, the mixing may be achieved by loading the renal tissue and polymer solution into a first container, such as a syringe, transferring the solution into another container, such as by expelling the contents of a syringe into a second syringe, transferring the solution back to the first container, and then repeating this cycle as necessary until a suspension is achieved.

After a suspension is formed, the suspension is extruded into bead-forming solution in order to form polymer beads within which the renal tissue is encapsulated. The extrusion may comprise ejecting the suspension from a syringe, or otherwise transferring the suspension from one container into another in which the bead-forming solution is contained, or alternatively, transferring the bead-forming solution into a container in which the suspension is held. The bead-forming solution may be ionic, may a cross-linking solution, or both. In one embodiment the bead-forming solution comprises $CaCl_2$. The polymer beads with encapsulated renal tissue may form spontaneously when combined with the bead-forming solution. The process of bead-forming may be further assisted, for example, by agitating the mixture of the suspension and the bead forming solution, modifying the temperature of the mixture (e.g., raising the temperature), or both.

Following the formation of the polymer beads, chemical cross-linking of the beads may be achieved by placing the beads into a cross-linking solution. For cross-linking, the beads may be transferred into a dilute solution of polymer, preferably a different polymer than the major polymer component of the beads. For example, if the major component of the polymer bead comprises alginate, a dilution solution of poly-L-lysine may be used to cross-link the alginate beads. Optionally, an additional polymer layer may be added to the polymer beads following their "production" in the bead-forming solution, or following cross-linking. Preferably, the additional polymer layer comprises the same polymer that makes up major component of the polymer beads. For example, an additional alginate layer may be added to a bead of which the major component is alginate. Adding another polymer layer to the polymer beads may be accomplished by placing the beads in a dilute polymer solution comprising the polymer of which the extra layer will be made.

The present invention is further defined in the following Examples. It should be understood that these examples, while indicating embodiments of the invention, are given by way of illustration only, and should not be construed as limiting the appended claims. From the above discussion and these examples, one skilled in the art can ascertain the essential characteristics of this invention, and without departing from the spirit and scope thereof, can make various changes and modifications of the invention to adapt it to various usages and conditions.

Example 1

Formation of Therapeutic Implant

Four kidneys from female, Long Evans rats (eight weeks old) were surgically removed, rinsed in ice cold phosphate buffered saline without $Ca^{2+}$ and $Mg^{2+}$ (PBS) (Invitrogen, Carlsbad, Calif.) and then, using a scalpel, were minced into small pieces (1-5 mm$^3$) A 300 uM-steel sieve (Sigma, St Louis, Mo.) was then used to further mince the tissue fragments. Minced tissue was then washed three times with 30-50 mL of Growth Medium containing Dulbecco's Modified Eagles Medium (DMEM) (Invitrogen) containing 1% penicillin/streptomycin (Invitrogen) and 1% fetal bovine serum (FBS) (Hyclone, Logan, Utah). The final wash was completely removed and the tissue fragments were loaded into one 1-milliliter syringe of a two syringe mixing system. A 1.8% (w/v) alginate solution (Sigma) was prepared in Growth Medium and was loaded into the second 1-milliliter syringe. The two solutions were then mixed together by pushing the contents back and forth through both syringes. The minced tissue-gel suspension was then extruded into a 100 mM $CaCl_2$ solution. The resulting encapsulated tissue beads were then incubated at room temperature in $CaCl_2$ with slow agitation for 5 minutes. The beads were then chemically cross-linked by transferring into 0.05% (w/v) poly-L-lysine, molecular weight 24,000 (Sigma) containing 1% FBS for 5 minutes and then coated with another layer of 0.1% (w/v) alginate solution containing 1% FBS for 5 minutes. Four to ten beads were then transferred to individual wells of a 24 well low-cluster, tissue culture dish containing 0.5 mL of Growth Medium, or Growth Media containing 100 ng/mL poly-D-glutamic acid (pDGA) (Sigma), and cultured at 37° C. for four days under either normoxic or hypoxic (5% Oxygen) atmospheric conditions. Beads were visually examined and imaged using a digital camera and Eclipse TE2000-U microscope (Nikon, Japan).

Visual examination of alginate encapsulated tissue beads showed that manual extrusion through the two-way syringe system was effective in generating spherical, tissue containing beads. Tissue fragments within the alginate beads were also visible, demonstrating a uniform distribution throughout the alginate gel.

Example 2

Bead Diameter Measurements

Fourteen individual, tissue containing beads were placed into a clean tissue culture plate and imaged using a Nikon dissecting microscope fitted with a digital camera. The diameter of each bead was then measured using IMAGE PRO PLUS Software.

Visual examination of alginate encapsulated tissue beads showed that manual extrusion through the two-way syringe system was effective in generating spherical, tissue containing beads. Tissue fragments within the alginate beads were also visible, demonstrating a uniform distribution throughout the alginate gel. One-hundred and fifteen beads were generated from 3.72 g of fragmented kidney tissue resulting in approximately 32 mg of tissue per bead. Table 1 shows the distribution of bead diameter.

TABLE 1

| Bead | Diameter (nm) |
|---|---|
| 1 | 4.84 |
| 2 | 4.26 |
| 3 | 4.66 |
| 4 | 4.13 |
| 5 | 4.37 |
| 6 | 4.13 |
| 7 | 4.83 |
| 8 | 4.59 |
| 9 | 4.36 |
| 10 | 4.42 |
| 11 | 4.34 |
| 12 | 5.90 |
| 13 | 4.55 |
| 14 | 4.51 |
| Average | 4.56 |
| Std | 0.44 |

The average diameter of fourteen individual beads was found to be 4.56+/−0.44 mm.

Example 3

Assessment of Cell Viability

Minced kidney tissue viability was assessed using ALAMAR BLUE (Invitrogen), a colorimetric REDOX indicator that is reduced in response to metabolic activity. After four days in culture, spent Growth Medium was removed from samples of non-encapsulated kidney tissue, encapsulated kidney tissue, isopropanol fixed kidney tissue and Growth Medium only. One milliliter of Growth Medium, containing 10% ALAMAR BLUE, was added to the samples and further incubated for 2-4 hours at 37° C., 5% $CO_2$ with gentle rocking. Spent media was then analyzed spectrophotometrically (SPECTRAMAX-190, Molecular devices, Sunnyvale, Calif.) at 570 nm and 600 nm. Media from each sample was analyzed in triplicate. Percent reduction of ALAMAR BLUE was determined following the manufactures instructions and is an indirect measurement of cell viability.

After four days of culture, tissue viability was evaluated. As compared to non-encapsulated tissue, encapsulation maintained greater tissue viability (FIG. 1). Non-encapsulated kidney tissue, cultured under either normoxia or hypoxia showed similar relative mean viabilities of 20.9%+/−3.4% and 21.0%+/−1.9%, respectively. However, encapsulated kidney tissue, cultured under normoxic conditions showed an increase in relative mean tissue viability. Encapsulated tissue showed a relative mean tissue viability of 83.5%+/−4.5%. Encapsulated kidney tissue, cultured under hypoxic conditions resulted in reduced tissue viability of 31.3%+/−3.4%. As expected, tissue fixation resulted in a significant decrease in tissue viability to 5.0%+/−0.084%.

Example 4

Epo Secretion Analysis

After four days of culture, spent media was collected and the amount of Epo released into the culture medium was determined using a Quantikine Mouse/Rat Erythropoietin ELISA kit (R&D systems, MN). The ELISA plate was assayed spectrophotometrically (SPECTRAMAX-190, Molecular devices, Sunnyvale, Calif.) at 540 nm. Data was analyzed by comparing absorbance values of unknown samples to the linear regression of a standard curve.

The amount of Epo released into the culture medium was determined on day 4 post-encapsulation by ELISA. Data was normalized to absorbance values obtained with Growth Medium only (Corrected Mean). Each measurement was conducted on spent media obtained from 8-10 beads. Standard error of the mean (SEM) was also calculated. Data shown in Table 2, below, is represented in graphical form in FIG. 2.

TABLE 2

| TREATMENT GROUP | MEAN (pg/mL) | SEM (pg/mL) | NORMALIZED MEAN (pg/mL) |
|---|---|---|---|
| Growth Medium only (background) | −26.79 | 3.73 | 0.00 |
| Beads only | −32.85 | 2.10 | −6.06 |
| Tissue only | 19.04 | 3.34 | 45.83 |
| Beads with tissue | 52.52 | 28.59 | 79.31 |
| Beads with tissue and pDGA | 34.12 | 10.50 | 60.91 |

Figure 2:
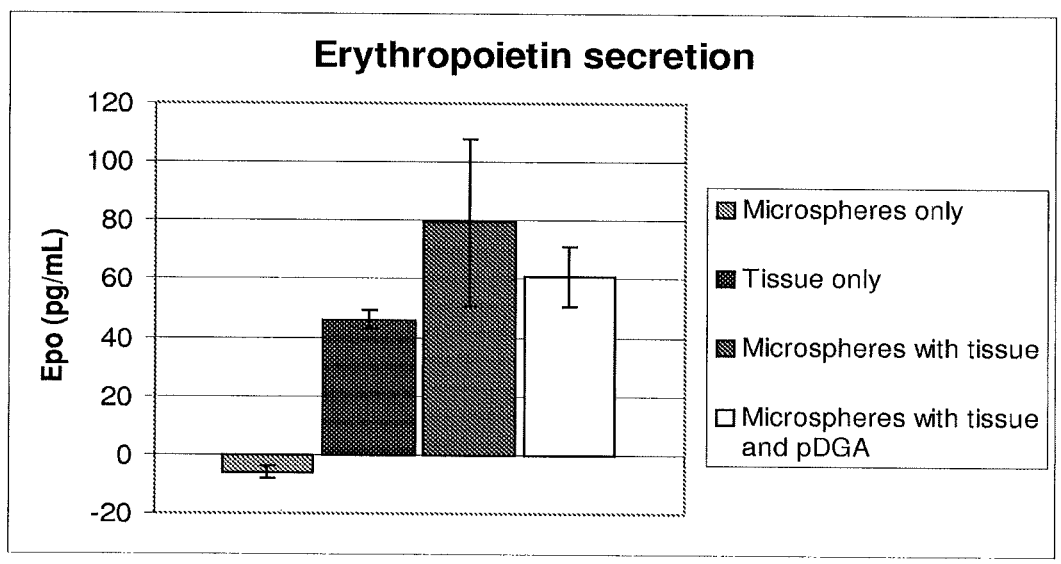
FIG. 2 illustrates the amount of Epo released into the culture medium, as determined on day 4 post-encapsulation by ELISA; data is included for beads devoid of tissue (beads only), non-encapsulated, minced rat kidney tissue (tissue only), and encapsulated, minced rat kidney tissue (beads with tissue).

In FIG. 2, data bars represent the average of triplicate measurements, and error bars represent SEM. Each measurement was conducted on spent media obtained from 8-10 beads.

Results showed that minced kidney tissue produced 45.8+/−3.3 pg/mL of Epo into the surrounding culture media. Likewise, alginate encapsulation did not impede Epo release from the minced tissue, producing 79.3+/−28.6 pg/mL of Epo. In order to determine if Epo production could be chemically enhanced, beads were prepared and cultured in pDGA. Results showed that pDGA treatment did not effect Epo production, generating 60.9+/−10.5 pg/mL of Epo. As a negative control, Epo production from beads devoid of tissue was determined. As expected, no measurable Epo was detected from these samples.

Example 5

Trophic Factor Secretion Analysis

After four days of culture, spent culture medium was harvested from the beads. Cell debris was removed from the spent culture medium by centrifugation and the culture medium was stored at −80° C. At the time of analysis, spent culture medium was assayed by ELISA for the following protein factors: interleukin-4 (IL-4), monocyte chemotactic protein-1 (MCP-1), RANTES, granulocyte-macrophage colony stimulating factor (GMCSF), interleukin-10 (IL-10), adiponectin, leptin, matrix metalloproteinase-2 (MMP-2) with Searchlight Proteome Arrays (Pierce Biotechnology Inc.).

As compared to spent culture medium derived from beads without tissue encapsulation, beads containing kidney tissue fragments secreted elevated amounts of MCP-1 (50.6+/−8.9 pg/mL), adiponectin (132,060.6+/−11,226.7 pg/mL), leptin (10.3+/−2.6 pg/mL) and MMP-2 (945.2+/−13.3 pg/mL) and low to undetectable amounts of IL-4, RANTES, GMCSF and IL-10. As shown in Table 3, below, each treatment group contained three samples (1, 2, 3).

TABLE 3

| | IL4 pg/ml | MCP1 pg/ml | RANTES pg/ml | GMCSF pg/ml | IL10 pg/ml | Adiponectin pg/ml | Leptin pg/ml | MMP2 pg/ml |
|---|---|---|---|---|---|---|---|---|
| Beads with tissue | | | | | | | | |
| 1 | 39.8 | 68.4 | 7.6 | 105.8 | 20.6 | 113137.8 | 14.6 | 1160.0 |
| 2 | 1.6 | 77.0 | 10.4 | 69.8 | 1.6 | 136667.8 | 19.6 | 1184.6 |
| 3 | 24.2 | 47.2 | 1.6 | 78.2 | 1.6 | 151719.0 | 10.6 | 1138.6 |
| AVG | 21.9 | 64.2 | 6.5 | 84.6 | 7.9 | 133841.5 | 14.9 | 1161.1 |
| STD | 19.2 | 15.3 | 4.5 | 18.8 | 11.0 | 19445.3 | 4.5 | 23.0 |
| SEM | 11.1 | 8.9 | 2.6 | 10.9 | 6.3 | 11226.7 | 2.6 | 13.3 |
| Beads without tissue | | | | | | | | |
| 1 | 32.0 | 14.4 | 1.6 | 63.8 | 13.4 | 1827.2 | 7.0 | 616.4 |
| 2 | 32.8 | 13.8 | 3.0 | 130.4 | 17.6 | 1655.2 | 5.1 | 15.6 |
| 3 | 32.6 | 12.6 | 1.8 | 118.2 | 18.8 | 1860.4 | 1.8 | 15.6 |
| AVG | 32.5 | 13.6 | 2.1 | 104.1 | 16.6 | 1780.9 | 4.6 | 215.9 |
| STD | 0.4 | 0.9 | 0.8 | 35.5 | 2.8 | 110.1 | 2.6 | 346.9 |
| SEM | 0.2 | 0.5 | 0.4 | 20.5 | 1.6 | 63.6 | 1.5 | 200.3 |
| Medium only | | | | | | | | |
| 1 | 29.0 | 3.1 | 1.6 | 98.8 | 20.4 | 939.2 | 5.1 | 15.6 |
| 2 | 30.2 | 22.6 | 1.6 | 91.2 | 16.6 | 1159.0 | 5.1 | 15.6 |
| 3 | 34.8 | 16.8 | 1.6 | 85.0 | 15.0 | 1436.4 | 2.0 | 441.8 |
| AVG | 31.3 | 14.2 | 1.6 | 91.7 | 17.3 | 1178.2 | 4.1 | 157.7 |
| STD | 3.1 | 10.0 | 0.0 | 6.9 | 2.8 | 249.2 | 1.8 | 246.1 |
| SEM | 1.8 | 5.8 | 0.0 | 4.0 | 1.6 | 143.8 | 1.0 | 142.1 |

Figure 3:
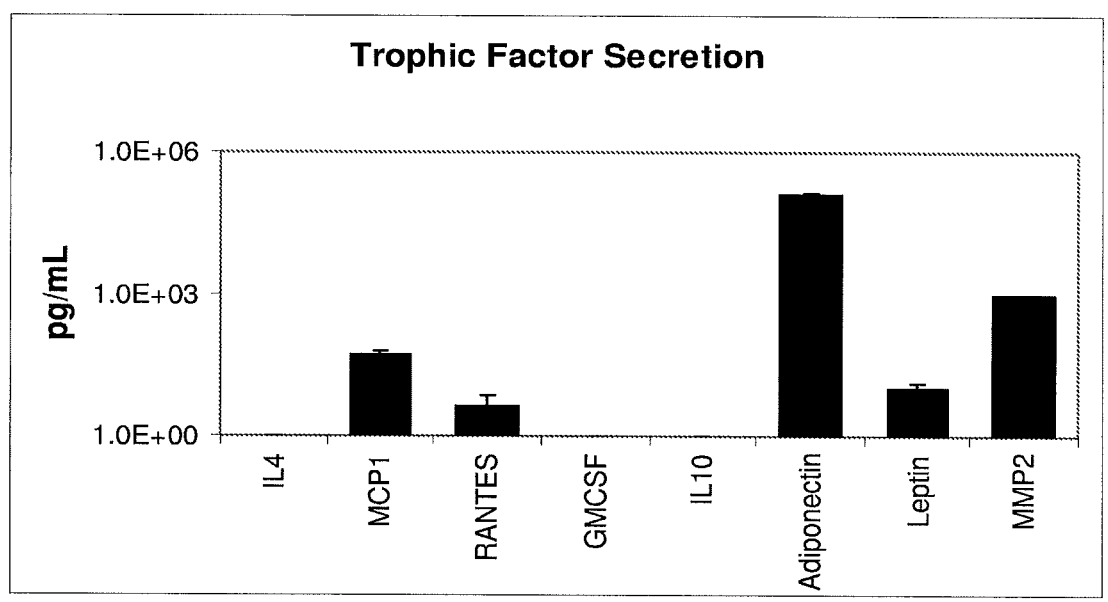
FIG. 3 depicts data from a study in which the average amount of various proteins secreted into the medium was measured after four days of culture.

STD=Standard deviation, SEM=Standard error of the mean. Data shown here is represented in graphical form in FIG. 3, in which data bars represent the average amount of protein secreted into the medium after four days of culture. Background measurements obtained from beads without tissue was subtracted from the data shown. Error bars represent SEM.

Example 6

Evaluation of Erythropoiesis Stimulating Activity

Rat erythroid CD34+ cells (Lonza, Walkersville Md.) are resuspended at 15,000 cells/cm2 in IMDM with 10% FBS. Bead conditioned medium are then added to methylcellulose colony forming assay medium (MethoCult GF H4534, StemCell Technologies, Vancouver BC). Cells are added to the methylcellulose and plated with subsequent incubation at 37° C., in a 5% $CO_2$ incubator for 12-14 days. Colonies containing over 50 cells are counted by phase contrast microscopy.

Conditioned media derived from encapsulated rat kidney tissue has previously been shown to contain Epo. Conditioned media is presently shown to have erythropoiesis stimulating activity (ESA) as measured by BFU-E activity.

Example 7

Evaluation of Renoprotective Effects of Encapsulated Renal Tissue Fragments The purpose of this study is to evaluate the renoprotective effects of alginate encapsulated rat kidney tissue fragments in a rat model of renal disease. Sprague Dawley rats (diabetic or non-diabetic) with an initial weight of 200-250 g are used for these experiments. The rats are anesthetized with an intraperitoneal injection (5 mg/kg) of a 4:1 solution of ketamine hydrochloride and xylazine hydrochloride. Kidney failure is induced by a two-stage nephrectomy procedure. The upper and lower parts of the left kidney (two thirds of one kidney) are resected using silk ligature while preserving the renal capsule. Ten days later, the right kidney is removed, leaving approximately ⅙ of the total kidney mass (5/6 nephrectomy). Applying soft pressure with methylcellulose stops bleeding, and the peritoneum and skin is closed in layers with resorbable 4-O Vicryl sutures.

Five weeks after the 5/6-nephrectomy procedure, beads are transplanted under the capsule as a control, 5/6 nephrectomized rats are injected with fibrin matrix only. Serum samples are obtained on days 0 (prior to 5/6 nephrectomy) and on day 1 (day of cell transplantation), days 7, 14, 21, 28 and 35 (day of necropsy). Blood urea nitrogen and creatinine are quantified using a VETACE CHEMISTRY ANALYZER (Alpha Wassermann Diagnostic Technologies, LLC, West Caldwell, N.J.).

Animals in all groups are sacrificed five weeks post cell transplantation by carbon dioxide asphyxiation. Kidneys are removed for histology and transcriptional analysis. Half of each kidney is snap-frozen in liquid nitrogen for RT-PCR analysis. Messenger RNA is isolated from the frozen kidney tissue by study coordinator and subjected to transcriptional analysis utilizing low-density microarray cards containing pro-fibrotic and inflammatory genes. The remaining corneal kidney section is fixed in 10% neutral buffered formalin for downstream histological analysis.

Kidney tissue fixed for histology will be histologically processed, sectioned (5 μm-thick) and stained with hematoxylin/eosin. Tubular injury is evaluated and scored by a veterinary pathology.

In this study, subcapsular transplantation of alginate encapsulated kidney tissue fragments will slow the progression of renal injury in 5/6 nephrectomized rodents or in rodent models of diabetic nephropathy. Both serum creatinine and blood urea nitrogen values are significantly reduced in the hUTC treated animals as compared to the control animals. In addition, the bead lowers blood glucose levels in rodent models of diabetic nephropathy. Histological injury assessment reveals a reduction in tubular necrosis and tubular dilation in the treated animals.

Despite the increasing interest in cell encapsulation as a method for delivering therapeutic agents, sparse to no attention has been placed on the encapsulation of whole tissue fragments. It has herein been demonstrated that encapsulated kidney tissue fragments secrete Epo and other beneficial agents into a culture medium. Therefore, the disclosed therapeutic implants and therapeutic methods can provide treatment of numerous disease states.

The disclosures of each patent, patent application and publication cited or described in this document are hereby incorporated herein by reference, in their entirety.

What is claimed:

1. A method for treating a disease state selected from the group consisting of anemia, stroke, cardiovascular disease, and renal disease in a subject comprising implanting a therapeutic implant comprising excised and minced fragments of whole renal tissue encapsulated in the presence of a growth medium within a polymer bead that is permeable to substances secreted by said tissue, wherein the fragments of whole renal tissue are obtained by a method consisting of excising and mincing whole renal tissue.

2. The method according to claim 1, wherein said renal tissue is autologous tissue, allogeneic tissue, xenogeneic tissue, or any combination thereof.

3. The method according to claim 1, wherein said fragments of whole renal tissue have a size of less than about 1 mm.

4. The method according to claim 1, wherein said fragments of whole renal tissue have a size of less than about 300 pm.

5. The method according to claim 1, wherein said therapeutic implant comprises at least about 30 mg of renal tissue.

6. The method according to claim 1, wherein said polymer bead comprises alginate, hyaluronic acid, carboxymethylcellulose, polyethylene glycol, dextran, agarose, poly-L-lysine, carageenan, pectin, tragacanth gum, xanthan gum, guar gum, gum arabic, type I collagen, laminin, fibronectin, fibrin, or any combination thereof.

7. The method according to claim 1, wherein said polymer bead comprises alginate and poly-L-lysine.

8. The method according to claim 1, wherein said polymer bead has a diameter of about 3 mm to about 6 mm.

* * * * *